United States Patent [19]
Thielemans et al.

[11] Patent Number: 5,741,806
[45] Date of Patent: Apr. 21, 1998

[54] SUPPOSITORY COMPOSITIONS CONTAINING ONDASETRON DIHYDRATE

[75] Inventors: Isabelle Thielemans; Isabelle Richard, both of Evreux, France

[73] Assignee: Laboratoire Glaxo Wellcome S.A., Paris, France

[21] Appl. No.: 537,950

[22] PCT Filed: May 24, 1994

[86] PCT No.: PCT/EP94/01652

§ 371 Date: Dec. 4, 1995

§ 102(e) Date: Dec. 4, 1995

[87] PCT Pub. No.: WO94/27599

PCT Pub. Date: Dec. 8, 1994

[30] Foreign Application Priority Data

May 25, 1993 [GB] United Kingdom ............... 9310756

[51] Int. Cl.⁶ .................................................. A61K 31/415
[52] U.S. Cl. ........................................................ 514/397
[58] Field of Search ............................................ 514/397

[56] References Cited

U.S. PATENT DOCUMENTS

| 4,695,578 | 9/1987 | Coates et al. | 514/397 |
| 4,983,621 | 1/1991 | Bunce et al. | 514/397 |

FOREIGN PATENT DOCUMENTS

| A-0 278 161 | 8/1988 | European Pat. Off. |
| A-2 633 831 | 1/1990 | France |
| WO-A-92 04012 | 3/1993 | WIPO |

OTHER PUBLICATIONS

Boylan et al., "Handbook of Pharmaceutical Excipients", 1986, American Pharmaceutical Association & The Pharmaceutical Society of Great Britain, pp. 314–320.

*Primary Examiner*—Raymond Henley, III
*Attorney, Agent, or Firm*—Bacon & Thomas

[57] ABSTRACT

The invention relates to a pharmaceutical composition for rectal administration which comprises 1,2,3,9-tetrahydro-9-methyl-3-[(2-methyl-1H-imidazol-1-yl)-methyl]-4H-carbazol-4-one in the form of its free base or a pharmaceutically acceptable solvate thereof as active ingredient, together with one or more pharmaceutically acceptable carriers or excipients. Methods for the manufacture of such compositions and for their use in the treatment of conditions mediated through the action of 5-hydroxytryptamine at 5-HT$_3$ receptors are also described.

6 Claims, No Drawings

SUPPOSITORY COMPOSITIONS CONTAINING ONDASETRON DIHYDRATE

This is a 371 of PCT/EP94/01652 filed May 24, 1994.

The present invention relates to a pharmaceutical composition containing, as active ingredient, 1,2,3,9-tetrahydro-9-methyl-3-[(2-methyl-1H-imidazol-1-yl)-methyl]-4H-carbazol-4-one, in particular a composition for rectal administration. 1,2,3,9-tetrahydro-9-methyl-3-[(2-methyl-1 H-imidazol-1-yl)-methyl]-4H-carbazol-4-one, which may be represented by the formula (I)

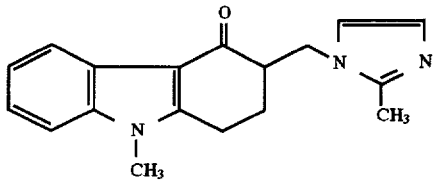

and its physiologically acceptable salts and solvates are disclosed in GB2153821. The compound of formula (I) is described as a potent and selective antagonist of 5-hydroxytryptamine (5-HT) at "neuronal" 5-HT receptors of the type located on terminals of primary afferent nerves. Receptors of this type are now designated as 5-HT$_3$ receptors and are also present in the central nervous system. 5-HT occurs widely in the neuronal pathways in the central nervous system and disturbance of these 5-HT containing pathways is known to alter behavioural syndromes such as mood, psychomotor activity, appetite and memory.

The compound is described as being of use in the treatment of a human or animal subject suffering from a condition caused by a disturbance of neuronal 5-HT function, for example in the treatment of a human subject suffering from migraine pain or a psychotic disorder such as schizophrenia. It is also stated that the compound may be useful in the treatment of conditions such as anxiety, obesity and mania.

Subsequently published patent applications disclose the use of the compound of formula (I) and other 5-HT$_3$ antagonists for the treatment of a number of other conditions such as dementia, cognitive disorders and emesis.

Numerous clinical studies have demonstrated the effectiveness of the compound of formula (I) for the treatment of emesis, particularly the nausea and vomiting associated with cancer chemotherapy and radiotherapy and that occurring post-operatively. Hitherto, the drug has always been administered in the form of a salt, in particular in the form of its hydrochloride dihydrate salt, either by injection or orally.

Oral administration constitutes the generally preferred route for administration of pharmaceuticals since this route is particularly convenient and acceptable to patients. Unfortunately oral compositions may be associated with certain disadvantages, particularly in the treatment of conditions accompanied by nausea and/or vomiting. It is highly desirable, particularly in the treatment of acute conditions, that pharmaceutical compositions have a rapid and consistent onset of action combined with sustained activity and good bioavailability. Rapid absorption can be achieved by parenteral injection but this is unacceptable to some patients, particularly if the drug is to be administered without direct medical supervision i.e. self-administered.

Alternative routes for administration of the compound of formula (I) are proposed in GB 2153821 including rectal administration. GB 2153821 specifically discloses a number of pharmaceutical formulations containing 1,2,3,9-tetrahydro-9-methyl-3-[(2-methyl-1H-imidazol-1-yl)-methyl]-4H-carbazol-4-one hydrochloride dihydrate as active ingredient and a specific suppository formulation for rectal administration containing this active ingredient has been disclosed in, for example, EP-0278161.

The present invention provides a particularly advantageous pharmaceutical formulation, not hitherto specifically disclosed, which is suitable for rectal administration of the compound of formula (I).

There is thus provided according to the invention a pharmaceutical composition for rectal administration which comprises 1,2,3,9-tetrahydro-9-methyl-3-[(2- methyl-1H-imidazol-1-yl)-methyl]-4H-carbazol-4-one in the form of its free base or a pharmaceutically acceptable solvate thereof as active ingredient, together with one or more pharmaceutically acceptable carriers or excipients.

Unlike the prior art compositions, the compositions according to the invention contain the active ingredient in the form of its free base or a pharmaceutically acceptable solvate thereof. The applicants have found that the use of the free base rather than the hydrochloride salt of the compound of formula (I) is surprisingly advantageous when the active ingredient is administered rectally.

The compositions according to the invention may be in the form of retention enemas, solid dosage forms such as suppositories or soft gelatin capsules, or semi solid dosage forms such as a rectal gel or cream. Preferably the compositions are formulated as solid unit dosage forms suitably shaped, for example conical, cylindrical or torpedo-shaped, for rectal administration. The solid dosage forms may either melt at body temperature or dissolve or disperse in the mucous secretions of the cavity.

Conventional carriers which may be employed in the compositions according to the invention include theobroma oil, hard fats, glycerides of fatty acids, glycerol-gelatin bases, macrogols (polyethylene glycols) and mixtures thereof. Preferred compositions comprise hard fat bases such as esterified, hydrogenated or fractionated vegetable oils and synthetic triglyceride mixtures produced under the name of adeps solidus.

Preferred hard fat bases are hard fats containing a mixture of mono-, di- and triglycerides of saturated $C_{9-18}$ fatty acids. Preferably the hard fat base comprises hard fats obtained by esterification of fatty acids of vegetable origin with glycerol, a macrogol ether containing 20 to 24 oxyethylene groups in the polyoxyethylene chain e.g. polyoxyl-20-cetostearyl ether, and glycerides e.g. glyceryl ricinoleate. Preferably the hard fat base has a high Hydroxyl Value (USP Chemical Test), for example a Hydroxyl Value of between 20 and 100, such as 40 to 80, in particular 60 to 70.

Solid dosage forms such as suppositories may be prepared in conventional manner for example by intimate admixture of the active ingredient with the carrier, preferably the molten carrier. Preferably the active ingredient is milled or sieved prior to incorporation into the molten carrier. The molten composition may then be poured into suitable moulds, for example PVC, polyethylene or aluminium moulds. Optionally the suppositories may be coated, prior to packing, for example with cetyl alcohol, macrogol or polyvinyl alcohol and polysorbates to increase disintegration time or lubrication or to reduce adhesion on storage.

Preferably the total weight of the solid dosage form is about 1 or 2 grams and the active ingredient may comprise 0.05 to 20% by weight of the compositon, preferably 0.1 to 20% by weight of the composition, more preferably 0.2 to 5% by weight of the composition, such as 0.4 to 3.2%.

The amount of 1,2,3,9-tetrahydro-9-methyl-3-[(2-methyl-1 H-imidazol-1-yl)- methyl]-4H-carbazol-4-one free base employed in the compositions of the invention will preferably be in the range of about 0.1 mg to about 100 mg, more preferably about 1 mg to about 50 mg, such as about 2 mg to about 35mg, for example about 5 mg to about 20 mg.

A further aspect of the invention provides a method of treating a mammal, including man, suffering from or susceptible to a condition mediated through the action of 5-hydroxytryptamine at 5-HT$_3$ receptors which comprises rectal administration of a pharmaceutical composition which comprises 1,2,3,9- tetrahydro-9-methyl-3-[(2-methyl 1 H-imidazol-1-yl)-methyl]-4H-carbazol-4-one in the form of its free base or a pharmaceutically acceptable solvate thereof as active ingredient, together with one or more pharmaceutically acceptable carriers or excipients. It will be appreciated that reference to treatment is intended to include prophylaxis as well as the alleviation of established symptoms.

Conditions mediated through the action of 5-HT at 5-HT$_3$ receptors include cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Impairment; psychotic disorders, such as schizophrenia and mania; anxiety disorders, including panic disorder, agoraphobia, social phobia, simple phobia, obsessive compulsive disorders, post traumatic stress disorder, mixed anxiety and depression, and generalised anxiety disorder; nausea and vomiting, particularly that associated with cancer chemotherapy and radiotherapy and also that occurring post operatively; irritable bowel syndrome and dependency on drugs and substances of abuse. Other conditions mediated in this manner include gastric stasis; symptoms of gastrointestinal dysfunction such as occur with peptic ulcer, reflux oesophagitis, flatulence and dyspepsia; migraine; obesity and conditions such as bulimia; pain; and depression.

The pharmaceutical compositions according to the invention have particular utility for the treatment of nausea and vomiting, particularly that associated with cancer chemotherapy and radiotherapy, but also that occurring post-operatively.

It will be appreciated that the precise therapeutic dose of the active ingredient will depend on the age and condition of the patient and the nature of the condition to be treated and will be at the ultimate discretion of the attendant physician.

However, in general, effective doses for the treatment of conditions mediated through the action of 5-hydroxytryptamine at 5-HT$_3$ receptors, for example postoperative nausea and vomiting will lie in the range of 0.1 to 200 mg, preferably 0.5 to 100 mg, most preferably 1 to 50 mg, for example 4, 8, 16 or 32 mg of the active ingredient per unit dose which could be administered in single or divided doses, for example, 1 to 4 times per day.

The invention is further illustrated by the following non-limiting examples.

EXAMPLE 1

| Suppository for Rectal Administration | |
|---|---|
| | Unit Formula (per suppository) |
| 1,2,3,9-Tetrahydro-9-methyl-3-[(2-methyl-1H-imidazol-1-yl)-methyl]-4H-carbazol-4-one (sieved free base) | 8 mg |
| Mixture of hard fats NF17, polyoxy-2-cetostearyl-ether NF17 and glyceryl ricinoleate (sold under the trade name Witepsol S58) Hydroxyl Value 60 to 70 | to 1 g |

EXAMPLES 2,3,4 and 5

Suppositories containing 1, 2, 4 or 16 mg 1,2,3,9-tetrahydro-9-methyl-3-[(2- methyl-1H-imidazol-1-yl)-methyl]-4H-carbazol-4-one (sieved free base) were prepared as described for the suppositories of Example 1.

EXAMPLE 6

| Suppository for Rectal Administration | |
|---|---|
| | Unit Formula (per suppository) |
| 1,2,3,9-Tetrahydro-9-methyl-3-[(2-methyl-1H-imidazol-1-yl)-methyl]-4H-carbazol-4-one (sieved free base) | 16 mg |
| Mixture of hard fats NF17, polyoxy-2-cetostearyl-ether NF17 and glyceryl ricinoleate (sold under the trade name Witepsol S58) Hydroxyl Value 60 to 70 | to 2 g |

EXAMPLES 7 and 8

Suppositories containing 8 or 32 mg 1,2,3,9-tetrahydro-9-methyl-3-[(2-methyl-1H-imidazol-1-yl)-methyl]-4H-carbazol-4-one (sieved free base) were prepared as described for the suppositories of Example 6.

EXAMPLE 9

Suppositories containing 4 mg 1,2,3,9-tetrahydro-9-methyl-3-[(2-methyl-1H-imidazol-1-yl)-methyl]-4H-carbazol-4-one (sieved free base) are prepared as described for the suppositories of Example 6.

We claim:

1. A pharmaceutical composition for rectal administration which comprises: 1,2,3,9-tetrahydro-9-methyl-3-[(2-methyl-1 H-imidazol-1-yl)-methyl]-4H-carbazol-4-one in the form of its free base or a pharmaceutically acceptable solvate thereof as active ingredient, together with a carrier; said carrier being a hard fat base having a hydroxy value range of 60–70; and said composition being in the form of a suppository.

2. A pharmaceutical composition as claimed in claim 1 which comprises 0.05 to 20% by weight of active ingredient.

3. A pharmaceutical composition as claimed in claim 1 which comprises 0.1 to 100 mg of active ingredient.

4. A method of treating a mammal, including man, suffering from or susceptible to a condition mediated through the action of 5-hydroxytryptamine at 5-HT$_3$ receptors which comprises rectal administration of a pharmaceutical composition in the form of a suppository wherein said suppository comprises 1,2,3,9-tetrahydro-9-methyl- 3-[(2-methyl-1H-imidazol-1-yl)-methyl]-4H-carbazol-4-one in the form of its free base or a pharmaceutically acceptable solvate thereof as active ingredient, together with a hard fat base carrier which has an hydroxy value range of 60–70.

5. A method according to claim 4 wherein the condition is nausea and vomiting.

6. A method as claimed in claim 4 wherein the pharmaceutical composition comprises 0.05 to 20% by weight of active ingredient.

* * * * *